United States Patent
Nie et al.

(10) Patent No.: US 12,431,245 B2
(45) Date of Patent: Sep. 30, 2025

(54) ATTENTION-BASED MULTIPLE INSTANCE LEARNING

(71) Applicants: Genentech, Inc., South San Francisco, CA (US); Hoffmann-La Roche Inc., Little Falls, NJ (US); Ventana Medical Systems, Inc., Tucson, AZ (US)

(72) Inventors: Yao Nie, Sunnyvale, CA (US); Xiao Li, Foster City, CA (US); Trung Kien Nguyen, Chelsea, MI (US); Fabien Gaire, Starnberg (DE); Eldad Klaiman, Starnberg (DE); Ido Ben-Shaul, Ramat Hasharon (IL); Jacob Gildenblat, Holon (IL); Ofir Etz Hadar, Hod Hasharon (IL)

(73) Assignees: Genentech, Inc., South San Francisco, CA (US); Hoffmann-La Roche Inc., Little Falls, NJ (US); Ventana Medical Systems, Inc., Tucson, AZ (US)

(*) Notice: Subject to any disclaimer, the term of this patent is extended or adjusted under 35 U.S.C. 154(b) by 285 days.

(21) Appl. No.: 18/139,873

(22) Filed: Apr. 26, 2023

(65) Prior Publication Data
US 2024/0079138 A1   Mar. 7, 2024

Related U.S. Application Data

(63) Continuation of application No. PCT/US2021/072166, filed on Nov. 1, 2021.

(60) Provisional application No. 63/108,659, filed on Nov. 2, 2020.

(51) Int. Cl.
| | |
|---|---|
| G16H 50/20 | (2018.01) |
| G06T 7/00 | (2017.01) |
| G16H 30/40 | (2018.01) |
| G06N 3/02 | (2006.01) |

(52) U.S. Cl.
CPC ........... G16H 50/20 (2018.01); G06T 7/0012 (2013.01); G16H 30/40 (2018.01); *G06N 3/02* (2013.01); *G06T 2207/20084* (2013.01)

(58) Field of Classification Search
None
See application file for complete search history.

(56) References Cited

U.S. PATENT DOCUMENTS

| | | | |
|---|---|---|---|
| 10,706,328 B2 * | 7/2020 | Stumpe | G06F 18/217 |
| 2018/0012356 A1 * | 1/2018 | Madabhushi | G06T 7/0012 |

(Continued)

FOREIGN PATENT DOCUMENTS

| | | |
|---|---|---|
| CN | 110223285 A | 9/2019 |
| CN | 111539491 A | 8/2020 |
| CN | 111709233 A | 9/2020 |

OTHER PUBLICATIONS

International Preliminary Report on Patentability, issued May 2, 2023, for PCT Application No. PCT/US2021/072166, filed Nov. 1, 2021, 12 pages.

(Continued)

*Primary Examiner* — Haris Sabah
(74) *Attorney, Agent, or Firm* — MORRISON & FOERSTER LLP

(57) ABSTRACT

Systems and methods relate to predicting disease progression by processing digital pathology images using neural networks. A digital pathology image that depicts a specimen stained with one or more stains is accessed. The specimen may have been collected from a subject. A set of patches are defined for the digital pathology image. Each patch of the set of patches depicts a portion of the digital pathology image. For each patch of the set of patches and using an attention-score neural network, an attention score is generated. The attention-score neural network may have been trained using a loss function that penalized attention-score variability (Continued)

across patches in training digital pathology images labeled to indicate no or low subsequent disease progression. Using a result-prediction neural network and the attention scores, a result is generated that represents a prediction of whether or an extent to which a disease of the subject will progress.

30 Claims, 5 Drawing Sheets

(56) References Cited

U.S. PATENT DOCUMENTS

| | | | | |
|---|---|---|---|---|
| 2018/0067179 A1* | 3/2018 | Madabhushi | ........ | G06V 10/772 |
| 2019/0087532 A1* | 3/2019 | Madabhushi | .... | G06V 30/19173 |
| 2019/0259156 A1* | 8/2019 | Madabhushi | ......... | G06T 7/0014 |

OTHER PUBLICATIONS

International Search Report and Written Opinion, mailed Feb. 28, 2022, for PCT Application No. PCT/US2021/072166, filed Nov. 1, 2021, 14 pages.

Liu, M. et al. (Apr. 3, 2020). "Histopathologic Cancer Detection by Dense-Attention Network with Incorporation of Prior Knowledge," 2020 IEEE 17th International Symposium on Biomedical Imaging, pp. 466-470.

Lu, M.Y. et al. (Oct. 24, 2019). "Semi-Supervised Histology Classification Using Deep Multiple Instance Learning and Contrastive Predictive Coding," Arxiv.org, 8 pages.

Yao, J. et al. (Jul. 19, 2020, e-pub. May 15, 2013). "Whole Slide Images Based Cancer Survival Prediction Using Attention Guided Deep Multiple Instance Learning Networks," Medical Image Analysis 16:1-15.

* cited by examiner

KL divergence to force uniform attention across tiles in negative slides (low risk patients): Hypothesis: no interesting signal in these slides KL divergence to force low attention to non-tumor regions

ATTENTION-BASED MULTIPLE INSTANCE LEARNING

CROSS-REFERENCE TO RELATED APPLICATION

This application is a continuation of International Application No. PCT/US2021/072166, filed on Nov. 1, 2021, which claims the benefit of and the priority to U.S. Provisional Application No. 63/108,659, entitled "ATTENTION-BASED MULTIPLE INSTANCE LEARNING" and filed on Nov. 2, 2020, which is hereby incorporated by reference in its entirety for all purposes.

FIELD

The present application generally relates to using attention-based techniques for processing digital pathology images. More specifically, an attention score and feature vector are generated for each of a set of patches, which can be processed by a neural network to generate a result (e.g., predictive of disease progression or used for risk stratification).

BACKGROUND

Lymphoid malignancies are the fourth most common cancers in both men and women and represent a significant healthcare burden. Diffuse large B-cell lymphoma (DLBCL) is the most common lymphoma subtype worldwide, accounting for 25-30% of non-Hodgkin's lymphoma in adults. Its incidence rises from two cases per 100,000 at 20-24 years of age, to 45 cases per 100,000 by 60-64 years, and 112 per 100,000 by 80-84 years. DLBCL is a highly heterogeneous disease in terms of disease biology and clinical outcomes and is categorized into distinct morphological, molecular, and immunophenotypic subtypes.

While in the front line setting, the current standard of care (SOC) regimen of rituximab, cyclophosphamide, doxorubicin, vincristine, and prednisone (R-CHOP) is highly successful in achieving cure in approximately 70% of patients and so far is not surpassed by other therapies, between 20% and 40% of patients do not respond to this regimen and are at high risk for unfavorable outcomes (such as disease progression, relapse, or death).

Currently, the most widely used prognostic score for identification of high risk patients in clinical practice and in clinical development is the International Prognostic Index (IPI) clinical score, first published in 1993 (before the introduction of immunotherapy (i.e., Rituximab)). The result generated by an index can be determined based on a disease stage, whether elevated levels of serum lactate dehydrogenase (LDH) were detected, whether the disease involved any extranodal sites, whether the disease involved more than one extranodal site, whether the disease involved both sides of the diaphragm, an ambulatory score (e.g., an Eastern Cooperative Oncology Group performance status), and/or an age of the subject. The IPI classifies subjects among three different levels of risk: low, low/intermediate, and high.

While indices, like the IPI, may provide prognostic indications regarding a subject or patient's disease survival, such indices currently cannot provide more details regarding their disease. At the same time, treatment may be administered based on a patient's risk of disease progression. For instance, a subject having a low risk of disease progression may receive a standard therapy, while a subject deemed to have a high risk for disease progression may receive an alternative treatment. IPI does not optimally discriminate the highly heterogeneous patient (sub)populations at risk for unfavorable clinical outcomes and cannot predict treatment benefits from a particular therapy.

There have been multiple attempts, utilizing modern technologies, to develop novel or IPI modified prognostic scores based on clinical, molecular, biological, radiological, and other risk factors. Exemplary prognostic scores include the Ann Arbor classification, an age-adjusted IPI, an enhanced version of the IPI (Revised-IPI, National Comprehensive Cancer Network IPI (NCCN-IPI)), molecular subtypes based on cell of origin (GCB/ABC), immunoexpression patterns (including, but not limited to, p53, Ki67, Bcl-2, Bcl-6, CD10, and CD5), Double Expressors, Double/Triple Hit (MYC/Bcl-6/Bcl-2), genomic profiling, prognostic mutation categories, and others.

There are other SOC regimens for identifying ultra-high risk DLBCL subjects, such as high baseline total metabolic tumor volume (TMTV) and the molecular definition of cell-of-origin (COO). One SOC tool that may be used for initial staging and determination of prognosis after treatment of DLBCL is interim PET.

However, none of these SOC regimes have achieved the required level of acceptance to be routinely used for risk stratification of DLBCL patients. Therefore, there remains a need for improving the IPI by developing new prognostic (and predictive) scores for risk stratification and identification of less-heterogeneous higher-risk groups with more precision.

SUMMARY

A computer-implemented method for using machine learning to process digital pathology images to predict disease progression is disclosed. The method comprises: accessing a digital pathology image that depicts a specimen stained with one or more stains, the specimen having been collected from a subject; defining a set of patches for the digital pathology image, wherein each patch of the set of patches depicts a portion of the digital pathology image; generating, for each patch of the set of patches and using an attention-score neural network, an attention score, wherein the attention-score neural network is trained using a loss function, the loss function penalizes attention-score variability across patches in training digital pathology images, the training digital pathology images labeled to indicate subsequent disease progression has occurred; generating, using a result-prediction neural network and the attention scores, a result representing a prediction of whether or an extent to which a disease of the subject will progress; and outputting the result.

Additionally or alternatively, in some embodiments, the method further comprises: generating, for each patch of the set of patches and using a feature-vector neural network, a feature vector for the patch, wherein the result further depends on the feature vectors for the set of patches.

Additionally or alternatively, in some embodiments, the result is an image-based output generated based on the feature vectors and the attention scores for the set of patches.

Additionally or alternatively, in some embodiments, the generating the result includes: generating a cross-patch feature vector using the feature vectors and the attention scores for the set of patches; and generating the result by processing the cross-patch feature vector using the result-prediction neural network.

Additionally or alternatively, in some embodiments, the feature vectors for the set of patches represent cell nuclei regions, wherein the generating the result further comprises: performing nuclei detection and segmentation to segment the set of patches into cell nuclei and non-cell nuclei regions; performing nuclei classification to identify individual cell nucleus from a nuclei segmentation mask; calculating cellular features from the set of patches and the nuclei segmentation mask; and calculating one or more patch-level metrics to form a patch-level representation, wherein the one or more patch-level metrics represent feature distribution of the cell nuclei regions.

Additionally or alternatively, in some embodiments, the feature-vector neural network includes a convolutional neural network.

Additionally or alternatively, in some embodiments, the loss function is configured to depend on multiple terms, wherein at least one of the multiple terms depends on an accuracy of the prediction and a second term defined.

Additionally or alternatively, in some embodiments, the loss function is defined using a K-L divergence technique.

Additionally or alternatively, in some embodiments, the loss function is configured such that a penalty depends on a degree of non-uniformity across the attention scores generated for the patches in the training digital pathology images labeled to indicate subsequent disease progression has occurred.

Additionally or alternatively, in some embodiments, the attention-score neural network includes a perceptron neural network.

Additionally or alternatively, in some embodiments, the attention-score neural network is trained using a training data set in which at least 90% of the training digital pathology images were labeled to indicate subsequent disease progression has occurred.

Additionally or alternatively, in some embodiments, the result represents a high likelihood of the disease of the subject progressing by at least a predefined threshold amount within a predefined period of time.

Additionally or alternatively, in some embodiments, the result further includes an identification of a subset of the set of patches that were more influential than other patches in the set of patches in the generation of result.

Additionally or alternatively, in some embodiments, the loss function further penalizes a lack of cross-portion variation in the attention scores in the training digital pathology images associated with no disease progression.

Additionally or alternatively, in some embodiments, the disease is at least one of: diffuse B-cell lymphoma, follicular lymphoma, chronic lymphocytic leukemia, small lymphocytic lymphoma, acute myeloid leukemia, or breast cancer.

A system for using machine learning to process digital pathology images to predict disease progression is disclosed herein, the system comprising one or more data processors, memory, and one or more programs stored in the memory for execution by the one or more processors and including instructions for performing steps of the methods described herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The present disclosure is described in conjunction with the appended figures.

Figure 1:
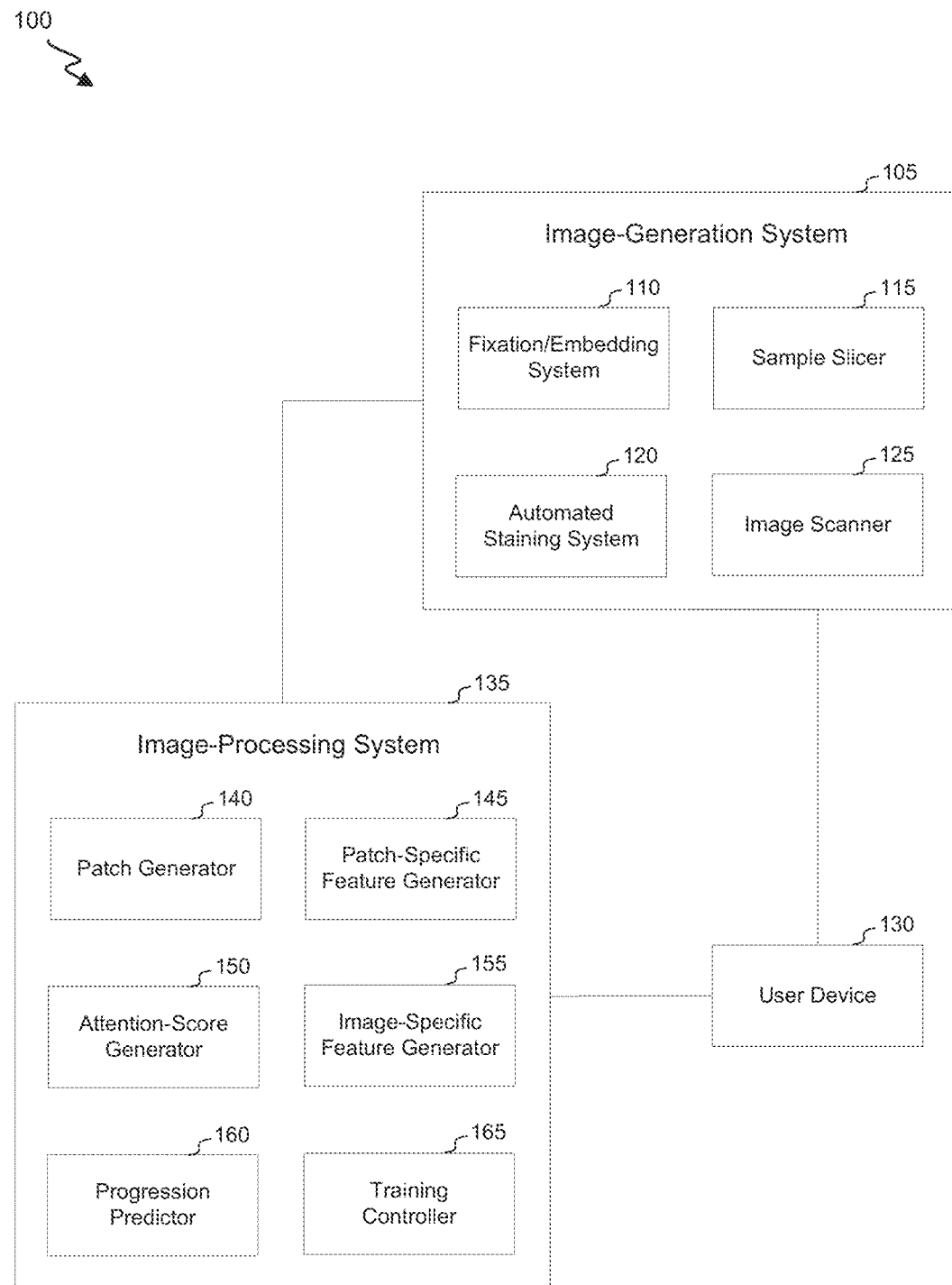
FIG. 1 shows a network of interacting computer systems for facilitating generating progression predictions using neural networks and attention-based techniques according to some embodiments of the present invention.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

I. Overview

Frequently, multiple treatment options are available to treat a given medical condition. A care provider and subject may select one treatment over another based on factors such as a current stage of disease, a predicted progression risk, and/or potential side effects. For example, if it is predicted that a particular subject's disease is likely to quickly and substantially progress, a treatment that is more aggressive (and has a higher adverse-event risk) may be selected over a less aggressive option.

Multiple indices have been developed to predict outcomes for subjects with non-Hodgkin's lymphoma (including DLBCL). In some instances, the progression risk may be predicted based on a current disease stage, a medical history (e.g., indicating whether the subject previously had the disease), age, and laboratory tests (e.g., a level of lactic acid dehydrogenase detected in blood of the subject).

The most widely used index, IPI, for predicting disease progression lacks precision, classifying patients in terms of aggressiveness of disease. The IPI is unsuitable for risk stratification and identification of heterogeneous higher-risk subjects. The IPI may not be able to predict treatment outcomes for a subject, making uncertain how and whether a patient may respond to a given type of therapy.

The techniques disclosed herein relate to, compute, or provide new prognostic and predictive scores for predicting disease progression and risk stratification with more precision than the IPI. The disclosed method makes a prediction based on a digital pathology image. Unlike IPI, results (scores) from the disclosed embodiments may be determined based on histomorphological features (tissue morphometrics) from digital pathology images. In some embodiments, the techniques may be combined with other prognostic tools (e.g., ctDNA, imaging, genomics, etc.) to develop composite prognostic scores.

The techniques may predict disease progression of a subject or refine patient classification. The techniques may also risk stratify subjects in anticipation of R-CHOP, Gazyva-CHOP (G-CHOP), Venetoclax-CHOP, or Polatuzumab-CHOP. The techniques may be used to identify high risk subjects (e.g., ultra-high risk DLBCL subjects or non-responders) for use in a clinical trial or to be treated with novel therapeutic options. For example, the high risk subjects may be patients likely to relapse or become refractory in two years (in 1L DLBCL R-CHOP patients). The identification of high risk subjects may allow the high risk subjects to benefit from being targeted for other therapies (such as new investigational products in clinical development, regimens other than R-CHOP in clinical practice (Polatuzumab (POLA) or Glofitamab), or intensified high dose chemotherapy). In this manner, the non-responders may not have to undergo exposure to therapies that the subject does not respond to and may experience less associated exposure to unknown toxicity.

The techniques may risk stratify DLBCL patients who will receive R-CHOP, G-CHOP, Venetoclax-CHOP, or Polatuzumab-CHOP therapy as first-line treatment. The scores may indicate the potential of relapse or becoming refractory within two years.

The results (scores) from the machine learning output may be used for designing clinic trials, resulting in time and cost savings. In some embodiments, the results may be used as an adjunct to standard patient characteristics and risk parameters to assist in designing faster and smaller clinical trials. For example, a score may be used to determine how frequently to order scans for patients in remission following treatment. As another example, the score may be used to determine the number of treatments or suggest alternative therapies, such as immunotherapy. By knowing information such as the frequency of scans or the number of treatments in advance, the time needed for investigating the dosage, administration schedule, etc. may be reduced.

Additionally or alternatively, by identifying high risk subjects that may benefit from alternative therapies, certain clinical trials may selectively choose and focus on these high risk subjects, thereby reducing its size. This may also create a demand for the development of these alternative therapies, e.g., for patients with high unmet need. In some instances, the identified high risk subjects may be more likely to experience a higher rate of particular events (e.g., disease progression, relapse, or death), and a clinical trial can be tailored accordingly. The higher rate of events may lead to a smaller patient population for enrollment and faster readout time, accelerating development timelines with faster market authorization. The score may enable more precise selection and/or stratification of high risk subjects with higher rate of particular events (e.g., disease progression, relapse, or death) in one or more phases (phase 3) of a study.

The results may also be used to determine cut off selections for designing clinical trials. The score of a given subject may determine which clinical trials a subject is eligible for. By identifying and more precisely selecting certain subjects, the techniques may result in reduced time needed for a clinical trial due to eliminating or reducing tissue analysis of subjects that do not meet the cut off criteria. For example, additional biomarker analysis may be avoided. Furthermore, the results may improve patient selection by, e.g., increasing the probability for technical success of a particular clinical trial with a particular molecule due to larger effect size.

Additionally or alternatively, the score may serve as a benchmark comparison for any newly developed prognostic factors and scores. In some embodiments, the score may be reviewed when evaluating a prospective clinical study.

The results may also be used to develop therapeutic options and new clinical development plans (CDPs). The results may be used to optimize planning, modeling, and simulations to predict whether a given CDP option is suitable for a new treatment. For example, the result may be used to determine the target population, or potential issues and bottlenecks in the development process. The techniques disclosed herein may serve as a modeling tool to inform the most efficient clinical study design, which may reduce the complexity of CDP decision making and accelerate clinical development. As one non-limiting example, the results may accelerate development of bispecific antibodies in DLBCL.

The techniques disclosed herein use machine learning or artificial intelligence to obtain more precision than IPI by detecting a level of detail beyond traditional H&E. The method may include using digital pathology images acquired at the time of diagnosis or before administration of therapy (e.g., R-CHOP). The training digital pathology images may be from a mixture of subjects that have relapsed, progressed, died, or undergone remission.

The method may use one or more neural networks to generate a feature vector and assign an attention score to each patch of multiple patches in the digital pathology image. The attention scores and feature vectors can be aggregated and processed (e.g., via another neural network) to generate an output corresponding to a predicted progression of a particular medical condition or outcome from a type of therapy. For example, an aggregate feature vector may be defined to be a weighted average of the patch feature vectors, with the weights being determined by or set to the attention scores. Training of the neural network(s) may facilitate detection of patches that are particularly predictive of progression or risk.

One complication in training neural networks to process digital pathology images to predict progression is that the training data set must include both "true" instances (where progression or risk was subsequently observed) and "false" instances (where progression or risk was not subsequently observed. The labels of digital pathology images may be binary (e.g., representative of whether, over a defined time period, any progression was observed; whether a threshold degree of progression was observed; or whether the subject survived for at least a predefined duration).

Even in the true instances, multiple portions of the image may depict normal biological environments. Thus, standard training may result in a neural network learning to associate normal biological environments with progression or risk, resulting in biases towards excessive predictions of the false instances or failure to learn the lower-level predictors of progression/risk.

Thus, some embodiments include training the neural networks using a training set of both censored and uncensored images, which can be identified by the labels of the images. A label includes a (time-to-event and an event type). The time-to-event identifies: (i) a time until occurrence of an event (e.g., until disease progression or death), or (ii) a time until a subject's data became unavailable (e.g., as a result of dropping out of a clinical study). In the first case (i), the event type is set to 1 (uncensored), while in the second case (ii), the event type is set to 0 (censored). Many uncensored images will include both patches predictive of progression and patches corresponding to normal biological environments.

II. Computing Network for Generating and Processing Digital Pathology Images

FIG. 1 shows a network 100 of interacting computer systems for facilitating generating progression (or risk) predictions using neural networks and attention-based techniques according to some embodiments of the present invention.

An image-generation system 105 can be configured to generate one or more digital pathology images corresponding to a particular sample. For example, an image generated by image-generation system 105 can include a stained section of a biopsy sample. As another example, an image generated by image-generation system 105 can include a slide image (e.g., a blood film) of a liquid sample.

Some types of samples (e.g., biopsies, solid samples and/or samples including tissue) can be processed by a fixation/embedding system 110 to fix and/or embed the sample. Fixation/embedding system 110 can be configured to facilitate infiltrating the sample with a fixating agent (e.g., liquid fixing agent, such as a formaldehyde solution) and/or embedding substance (e.g., a histological wax). For example, a fixation sub-system can fixate a sample by exposing the sample to a fixating agent for at least a threshold amount of time (e.g., at least 3 hours, at least 6 hours, or at least 12 hours). A dehydration sub-system can dehydrate the sample (e.g., by exposing the fixed sample and/or a portion of the fixed sample to one or more ethanol solutions) and potentially clear the dehydrated sample using a clearing intermediate agent (e.g., that includes ethanol and a histological wax). An embedding sub-system can infiltrate the sample (e.g., one or more times for corresponding predefined time periods) with a heated (e.g., and thus liquid) histological wax. The histological wax can include a paraffin wax and potentially one or more resins (e.g., styrene or polyethylene). The sample and wax can then be cooled, and the wax-infiltrated sample can then be blocked out.

A sample slicer 115 can receive the fixed and embedded sample and can produce a set of sections. Sample slicer 115 can expose the fixed and embedded sample to cool or cold temperatures. Sample slicer 115 can then cut the chilled sample (or a trimmed version thereof) to produce a set of sections. Each section may have a thickness that is (for example) less than 100 µm, less than 50 µm, less than 10 µm, or less than 5 µm. Each section may have a thickness that is (for example) greater than 0.1 µm, greater than 1 µm, greater than 2 µm, or greater than 4 µm. The cutting of the chilled sample may be performed in a warm water bath (e.g., at a temperature of at least 30° C., at least 35° C. or at least 40° C.).

An automated staining system 120 can facilitate staining one or more of the sample sections by exposing each section to one or more staining agents. Each section may be exposed to a predefined volume of staining agent for a predefined period of time. In some instances, a single section is concurrently or sequentially exposed to multiple staining agents.

Each of one or more stained sections can be presented to an image scanner 125, which can capture a digital image of the section. Image scanner 125 can include a microscope camera. Image scanner 125 may be further configured to capture annotations and/or morphometrics identified by a human operator. In some embodiments, the images may be from multiple scanners with various depths of metadata.

In some instances, a section is returned to automated staining system 120 after one or more images are captured, such that the section can be washed, exposed to one or more other stains, and imaged again. When multiple stains are used, the stains may be selected to have different color profiles, such that a first region of an image corresponding to a first section portion that absorbed a large amount of a first stain can be distinguished from a second region of the image (or a different image) corresponding to a second section portion that absorbed a large amount of a second stain.

It will be appreciated that one or more components of image-generation system 105 may, in some instances, operate in connection with one or more human operators. For example, a human operator may move the sample across various sub-systems (e.g., of fixation embedding system 110 or of image-generation system 105) and/or initiate or terminate operation of one or more sub-systems, systems, or components of image-generation system 105. As another example, part or all of one or more components of image-generation system (e.g., one or more sub-systems of fixation-embedding system 110) may be partly or entirely replaced with actions of a human operator.

Further, it will be appreciated that, while various described and depicted functions and components of image-generation system 105 pertain to processing of a solid and/or biopsy sample, other embodiments can relate to a liquid sample (e.g., a blood sample). For example, image-generation system 105 may be configured to receive a liquid-sample (e.g., blood or urine) slide that includes a base slide, smeared liquid sample, and a cover. Image scanner 125 can then capture an image of the sample slide.

A given sample may be associated with one or more users (e.g., one or more physicians, laboratory technicians and/or medical providers). An associated user can include a person who ordered a test or biopsy that produced a sample being imaged and/or a person with permission to receive results of a test or biopsy. For example, a user can correspond to a physician or a subject (from whom a sample was taken) him/herself. A user can use one or one user devices 130 to (for example) initially submit one or more requests (e.g., that identify a subject) that a sample be processed by image-generation system 105 and that a resulting image be processed by an image-processing system 135.

Thus, in some instances, the image-generation system 105 transmits an image produced by image scanner 125 to user device 130, and the user device 130 communicates with the image-processing system 135 to initiate automated processing of the image. In some instances, the image-generation system 105 avails an image produced by the image scanner 125 to the image-processing system 135 directly.

Image-processing system 135 can be configured to process digital pathology images to predict disease progression. A patch generator 140 can define, for each received image, a set of patches. In various instances, the patches may be non-overlapping or overlapping. In some instances, the patch generator 140 is configured to define a set of patches for an image where each patch is of a predefined size and/or an offset between patches is predefined. A patch size and/or patch offset may be determined by (for example) calculating one or more performance metrics (e.g., precision, recall, accuracy, and/or error) for each size/offset, and by selecting a patch size and/or offset associated with one or more performance metrics above a predetermined threshold and/ or associated with one or more best (e.g., high precision, highest recall, highest accuracy, and/or lowest error) performance metric(s).

In some instances, the patch generator 140 is configured to define a set of patches for an image where a number of patches in the set is predefined. In some instances, a patch size and an adjacent-patch overlap are predefined, such that a number of patches to be included in the set can be determined based on a size of an image, the patch size, and the adjacent-patch overlap.

A patch-specific feature generator 145 can be configured to generate, for each patch, a feature vector. Patch-specific feature generator 145 may use a neural network (e.g., a convolutional neural network) to generate a feature vector that represents each patch of the image. The neural network may include a network configured to receive a vector corresponding to a set of pixel intensities. The neural network may have been trained to learn features that facilitate predicting the risk score of the patient, e.g., if subject A has disease progression earlier than subject B, the model is trained to produce a higher risk score for subject A as compared to subject B. The risk score reflects the labels described throughout. In some embodiments, the risk score may be based on histomorphological features (tissue morphometrics). The histomorphological features may be obtained from H&E digitized slides.

An attention-score generator 150 can be configured to generate, for each patch, an attention score. The attention score may be (for example) defined to be and/or interpreted to be an extent to which a given patch is predictive of an output. It will be appreciated that an attention score is not defined to be a particular static value for a given patch. Rather, image-related details (e.g., intensities and/or color values) within the patch may be processed to determine the attention score for the patch (e.g., potentially in combination with a position of the patch). Attention-score generator 150 may generate attention scores using (for example) another neural network. The other neural network may include a network configured to receive a vector corresponding to a set of pixel intensities. The other neural network may include a feedforward network, a perceptron network (e.g., a multilayer perceptron), and/or a network having one or more fully connected layers. In some instances, the other neural network includes a convolutional neural network and one or more additional layers (e.g., a fully connected layer).

An image-specific feature generator 155 may generate a feature vector for the image using the patch-specific feature vectors and the patch-specific attention scores. A patch-specific feature vector may include one or more features that indicate and/or correspond to a size of depicted objects (e.g., sizes of depicted cells) and/or a density of depicted objects (e.g., a density of depicted cells). With respect to a high-risk slide and/or a high-risk subject, one or more patches can be associated with a patch-specific feature vector that represents large and/or dense cells, while a patch-specific feature vector that represents a patch associated with a low-risk slide and/or with a low-risk subject may lack such features. That is, the neural network used to generate patch-specific feature vectors may have learned that features that represent whether a patch depicts large and/or dense cells are informative in predicting an outcome of a corresponding subject. Patches associated with feature vectors representing large and/or dense cells may be associated with high attention scores. That is, the other neural network used to generate attention scores may have learned that high attention is to be assigned to feature vectors representing depictions of large and/or dense cells.

With respect to a low-risk slide and/or low-risk subject, one or more patches can be associated with a patch-specific feature vector that represents stroma, connective tissue, and/or cell nuclei regions. That is, the neural network used to generate patch-specific feature vectors may have learned that features that represent whether a patch depicts stroma, connective tissue, and/or cell nuclei regions are informative in predicting an outcome of a corresponding subject. Patches associated with feature vectors representing stroma, connective tissue, and/or cell nuclei regions may be associated with low attention scores. That is, the other neural network used to generate attention scores may have learned that high attention is to be assigned to feature vectors representing depictions of stroma, connective tissue, and/or cell nuclei regions.

In generating the patch-specific feature vectors representing cell nuclei regions, the patches may be analyzed by initially performing nuclei detection and segmentation, and nuclei classification using deep learning neural network models. The nuclei detection and segmentation algorithm may segment the set of patches into foreground (cell nuclei) and background (non-cell nuclei) regions. The nuclei classification algorithm may identify individual cell nucleus from a nuclei segmentation mask. The nuclei segmentation mask may be a binary nuclei segmentation mask, for example. For each individual nucleus, the nuclei classification algorithm may extract a small image patch and classify the individual cell nucleus into one or more categories (e.g., tumor, lymphocytes, etc.).

A set of cellular features from each individual nucleus may be calculated using the original patch and the nuclei segmentation mask. Exemplary cellular features may include, but are not limited to, chromatin distribution features, geometric coordinates, basic morphology features, shape-based features, first order statistics of gray intensity inside the nuclei, gray level co-occurrence matrix, gray level dependence matrix, gray level run length matrix, gray level size zone matrix, neighboring gray tone difference matrix, advanced nucleus morphology features, boundary signature features, and curvature features.

In some embodiments, one or more patch-level metrics may be calculated to form a patch-level representation. The patch-level metrics may describe the feature distribution for all the cell nuclei regions in each image patch. Dimensions for an image patch may be, for example, 256×256 pixels or 512×512 pixels. Exemplary patch-level metrics may include, but are not limited to, tumor cell density, lymphocyte density, and cell area uniformity. The patch-level representation may be input into a multi-instance learning (MIL) network. The MIL network may comprise attention layers and classification layers.

In some instances, the patch-specific feature vectors and the patch-specific attention scores are processed to generate an aggregate feature vector. For example, a weighted average feature vector may be generated by weighting the patch-specific feature vectors using the attention scores, and then summing the weighted patch-specific feature vectors. In some instances, the attention scores are transformed using a function (e.g., a sigmoidal function), and the transformed scores are used to weight patch-specific feature vectors.

A progression predictor 160 may then process the aggregate feature vector to generate a result that may have fewer dimensions and/or fewer numbers than the aggregate feature vector. For example, the result may be a single number, while the aggregate feature vector may include multiple numbers. The aggregate feature vector may be processed using a neural network, such as a feedforward network, perceptron network (e.g., a multilayer perceptron), and/or a network having one or more fully connected layers. An activation function (e.g., logistic function, sigmoidal function, tanh function, or step function) may be used to convert an output from the neural network to (for example) a number within a predefined range (e.g., between 0 and 1) or a binary value.

The result generated by the progression predictor 160 may correspond to a prediction pertaining to progression of a particular medical condition (e.g., a particular type of cancer) or associated risks for a particular subject associated with the digital pathology image. The result may correspond to a prediction as to (for example) whether the medical condition will progress over a predefined time, a degree to which the medical condition will progress over a predefined time period, and/or a speed the medical condition will progress. The result may correspond to a prediction as to (for example) whether the subject will survive for at least a predefined time period and/or whether progression-free survival will be observed in the subject for at least a predefined time period. In some embodiments, the result may correspond to a risk determined based on detection of stroma, connective tissue, and/or cell nuclei regions.

In some embodiments, the result may correspond to a prediction as to (for example) whether subject will respond to a certain treatment. The result may be used to identify high risk subjects in anticipation of R-CHOP, G-CHOP, Venetoclax-CHOP, or Polatuzumab-CHOP; or high risk non-responders to R-CHOP, G-CHOP, Venetoclax-CHOP, or Polatuzumab-CHOP. In some embodiments, the result may be used to identify ultra-high risk DLBCL subjects. In some embodiments, the result may indicate likelihood of relapsing or becoming refractory in a time period (e.g., two years) (in 1$s$ t line setting DLBCL R-CHOP patients).

The system 100 may provide a subject having a high risk for progression with an indication or recommendation an alternative treatment, such as (for example) intensified high dose chemotherapy or experimental new treatments. Exemplary non-limiting alternative treatments may include an autologous stem cell transplant, intrathecal chemotherapy, targeted therapy (e.g., selinexor), alternative chemotherapy (e.g., Polatuzumab), anti-CD20 chemotherapy (e.g., Gazyva), BCL2 inhibitors (e.g., Venetoclax), a monoclonal antibody, or therapy being investigated in a clinical study.

A training controller 165 can control training of one or more models (e.g., the neural network used to generate patch-specific feature vectors and/or the other neural network used to generate attention scores) and/or functions used by image-processing system 135. In some instances, multiple or all of the neural networks used by image-processing system 135 (e.g., the neural network used to generate patch-specific attention scores, the other neural network used to generate patch-specific feature vectors, and/or a neural network used to generate an image-specific feature vector) are trained together by the training controller 165.

Training controller 165 may select, retrieve, and/or access training data that includes a set of digital pathology images. The training data may further include a corresponding set of labels. Each label may correspond a data type of a result. For example, if the progression predictor 160 is configured to output a result that predicts whether a subject would exhibit progression-free survival for two years, the label may similarly indicate whether progression-free survival of at least two years was observed for another subject represented in the training data.

In some instances, the training controller 165 preferentially selects, retrieves, and/or accesses training digital pathology images associated with a particular label. Thus, a training data set may be biased toward or unbalanced towards digital pathology images associated with the particular label. The training data set may be defined to include more digital pathology images associated with labels indicating no progression (e.g., across a given time period) relative to digital pathology images associated with labels indicating progression occurrence (e.g., across the given time period). The training data set may be defined to include more digital pathology images associated with labels indicating survival (e.g., overall survival during a predefined time period or progression-free survival during a predefined time period) relative to digital pathology images associated with labels indicating a lack of survival. In some instances, the training data set is defined to only include digital pathology images associated with labels indicating no progression across a given time period or indicating survival (e.g., overall survival or progression-free survival) across a given time period. In some instances, the training data set is defined such that the set lacks or does not include digital pathology images associated with labels indicating progression across a given time period, indicating a lack of survival, or indicating death.

Training controller 165 may use a loss function that penalizes variability or differences in attention scores across patches (e.g., in a given image or in the training data set). In some instances, the loss function is configured to penalize differences between a distribution of patch-specific attention scores (associated with a single image or in the training data) and a reference distribution. The reference distribution may include (for example) a delta distribution (e.g., a Dirac delta function), a uniform distribution, or a Gaussian distribution. Preprocessing of the reference distribution and/or the attention-score distribution may be performed, which may include (for example) shifting one or both of the two distributions to have a same center of mass, a same median, or a same average. It will be appreciated that, alternatively, attention scores may be preprocessed prior to generating the distribution. The loss function may be configured to characterize the differences between the distributions using (for example) K-L divergence. If the attention-score distribution included multiple disparate peaks, the divergence with a delta distribution or uniform distribution may be more dramatic, which may result in a higher penalty.

In some instances, the training controller 165 uses a loss function that penalizes multimodality of a distribution of attention scores generated for patches of a given image. In some instances, the training controller 165 uses a loss function in which a penalty or cost is correlated with a standard deviation or variance across patch-specific attention scores for a given image.

It will be appreciated that an additional or alternative technique may use a loss function that penalizes a lack of variability across patch-specific attention scores for images associated with labels indicating that progression was observed and/or that the subject did not survive during a predefined time period. For example, a loss function may be configured to scale a penalty in an inverse manner to a K-L divergence between an attention-score distribution and a delta or uniform distribution. Thus, in some instances, different types (e.g., opposite types) of loss are used for images associated with different labels.

A result generated by the image-processing system 135 for a given subject may be transmitted to user device 130. The result may correspond to a prediction related to progression (which may include a prediction related to survival) or risk stratification. The result may be used to (for example) inform a treatment selection, inform a treatment recommendation, inform whether the subject is eligible for a clinical study, inform assignment of the subject to a treatment arm in a clinical study, and/or information of the need for investigating new products or regimens other than R-CHOP, G-CHOP, Venetoclax-CHOP, or Polatuzumab-CHOP. The generated resulted may assist in designing faster and smaller clinical trials, along with reduced costs and complexity associated with CDP decision making.

For example, a result may be used to predict whether the subject is at high risk for disease progression. More specifically, if a result predicts that progression is likely and/or that survival is unlikely if no treatment is provided or if a first line treatment is provided, it may be determined that the subject is at high risk. In some instances, progression predictor 160 compares a result to a threshold to predict whether the subject is at high risk for disease progression. In some instances, a result is accompanied by an interpretable scale description that may include a predicted probability of progression (e.g., any type of progression or of death) for a predefined time period for each of a set of ranges along a scale.

When it is predicted that a subject is at low risk for progression or unfavorable treatment outcome, a traditional R-CHOP therapy may be recommended, selected, or used. When it is predicted that a subject is at high risk for progression or unfavorable treatment outcome, an alternative treatment may be recommended, selected, or used. An alternative treatment may include (for example) an autologous stem cell transplant, intrathecal chemotherapy, targeted therapy (e.g., selinexor), alternative chemotherapy (e.g., Polatuzumab), anti-CD20 chemotherapy (e.g., Gazyva), BCL2 inhibitors (e.g., Venetoclax), a monoclonal antibody, or therapy being investigated in a clinical study.

Thus, noisy and unbalanced data sets may include individual images that include depictions of both healthy tissue and of tumor and/or immune cells that may predict a course of a disease. Further, the data set may be unbalanced and include more patches that do not include depictions of any disease activity than patches that do. Thus, there is a risk of a model learning to associate depictions of healthy tissue with a prediction of progression or death (due to the labels being at a subject level and applying to the whole image).

However, techniques disclosed herein use a combination of neural networks to generate patch-specific feature vectors and patch-specific attention values to facilitate processing of noisy and unbalanced data sets to generate accurate predictions. More specifically, using multiple neural networks to generate the patch-specific feature vectors and patch-specific attention values can reduce the likelihood that portions of images that do not depict cancerous activity or cancerous tissue are interpreted as being predictive of progression or death. Thus, techniques disclosed herein can generate predictions of high specificity (where instances of no progression or of survival are correctly predicted). Further, because these techniques can further facilitate detecting features that actually do correspond to subsequent progression or death, the techniques can also generate predictions of high sensitivity (where instances of progression or of death are correctly predicted).

III. Exemplary Process Flow for Processing Digital Pathology Images

Figure 2:
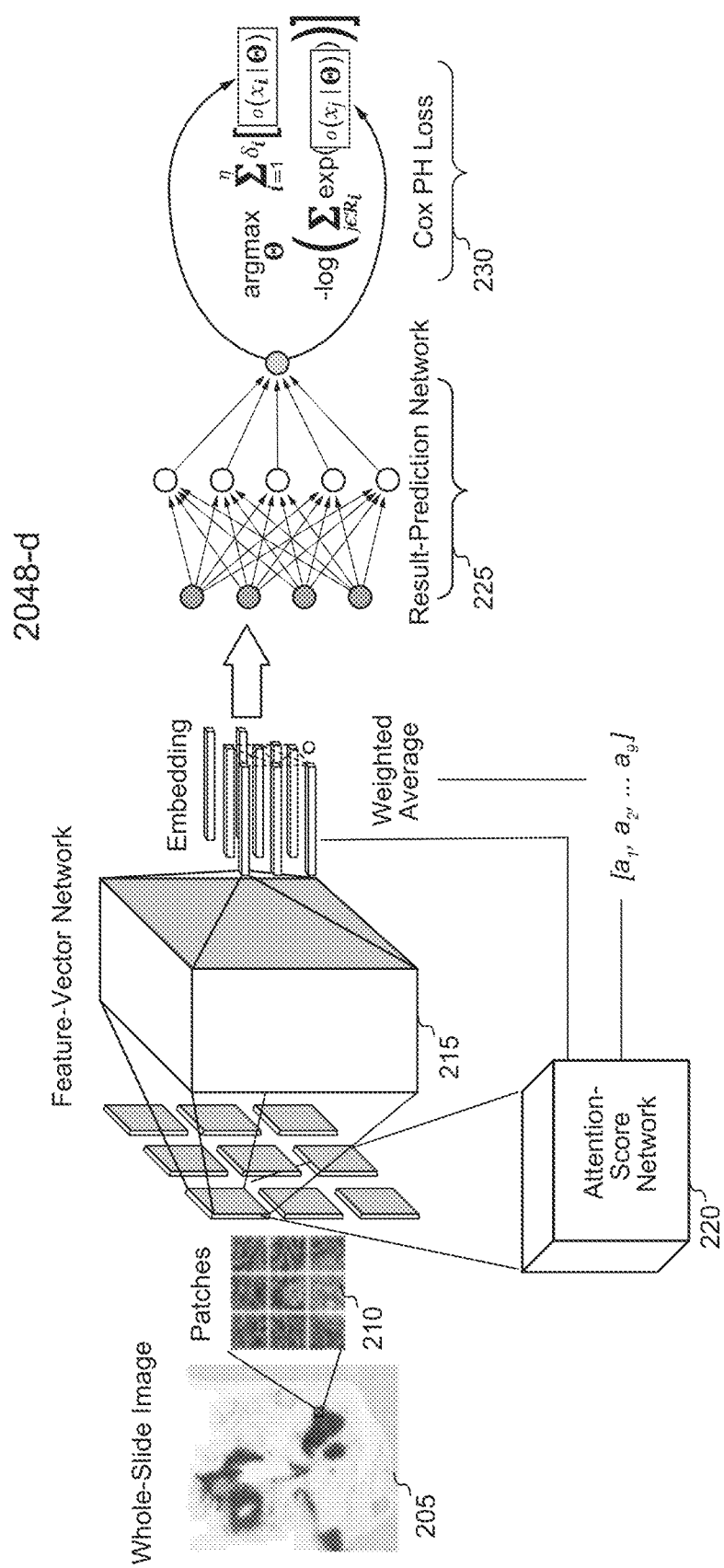
FIG. 2 illustrates a process flow for processing digital pathology images using multiple neural networks according to some embodiments of the present invention.

FIG. 2 illustrates a process flow 200 for processing digital pathology images using multiple neural networks according to some embodiments of the present invention. Process flow 200 may be performed by image-processing system 135. An input image can include a digital pathology image 205. Digital pathology image 205 may include an image of a slice of a sample. The sample may have been stained with one or more stains, such as an antibody to CD10, bcl-6, MUM1, FOXP1, cyclin D2, H&E, immunohistochemistry (IHC), and/or bcl-2.

A set of patches 210 can be generated (e.g., by patch generator 140) using WS image 205. In some instances, the patches are non-overlapping. In some instances, the patches are overlapping. Each patch may be of a uniform and predefined size.

Each patch can be processed by a feature-vector network 215 and by an attention-score network 220. For example, the patch-specific feature generator 145 can use the feature-vector network 215 to generate a patch-specific feature vector, and the attention-score generator 150 can use the attention-score network 220 to generate a patch-specific attention score. Feature-vector network 215 may include a convolutional neural network and may be configured to generate a feature vector. Attention-score network 220 may include a feedforward neural network (e.g., a multilayer perceptron) and may be configured to generate an attention score. The attention score may represent an extent to which the patch is predicted to include features that are particularly informative as to a progression (or risk) prediction and/or that are particularly predictive of progression (or risk).

The feature vectors and attention scores can be aggregated (e.g., by image-specific feature generator 155) to generate an aggregate feature vector. The attention scores may serve as weights that weight patch-specific feature vectors.

The aggregate feature vector can be fed to a result-prediction network 225 (e.g., part or all of progression predictor 160). Result-prediction network 225 may include one or more hidden layers and/or one or more fully connected layers. The feature vector may have a predefined dimension, such as a [1, 2048] dimensionality.

A Cox proportional-hazard loss (Cox PH loss 230) can be used (e.g., by training controller 165) to train networks 215, 220 and 225. The result prediction network can generate a risk score for each cross-patch image (e.g., specific to a subject). During the training stage, in each mini-batch (including multiple subjects), a result (e.g., risk score) of each subject can be computed using the current state of the network. The Cox PH loss 230 can be applied to increase the score of the patients at higher risk (patients with actual disease progression event) with respect to scores of patients at lower risk (patients whose events occur later). By doing this, the network can learn to predict the risk scores of the patients in test phase, e.g., patients with higher predicted risk scores are considered higher risk (shorter time to event).

Figure 3:
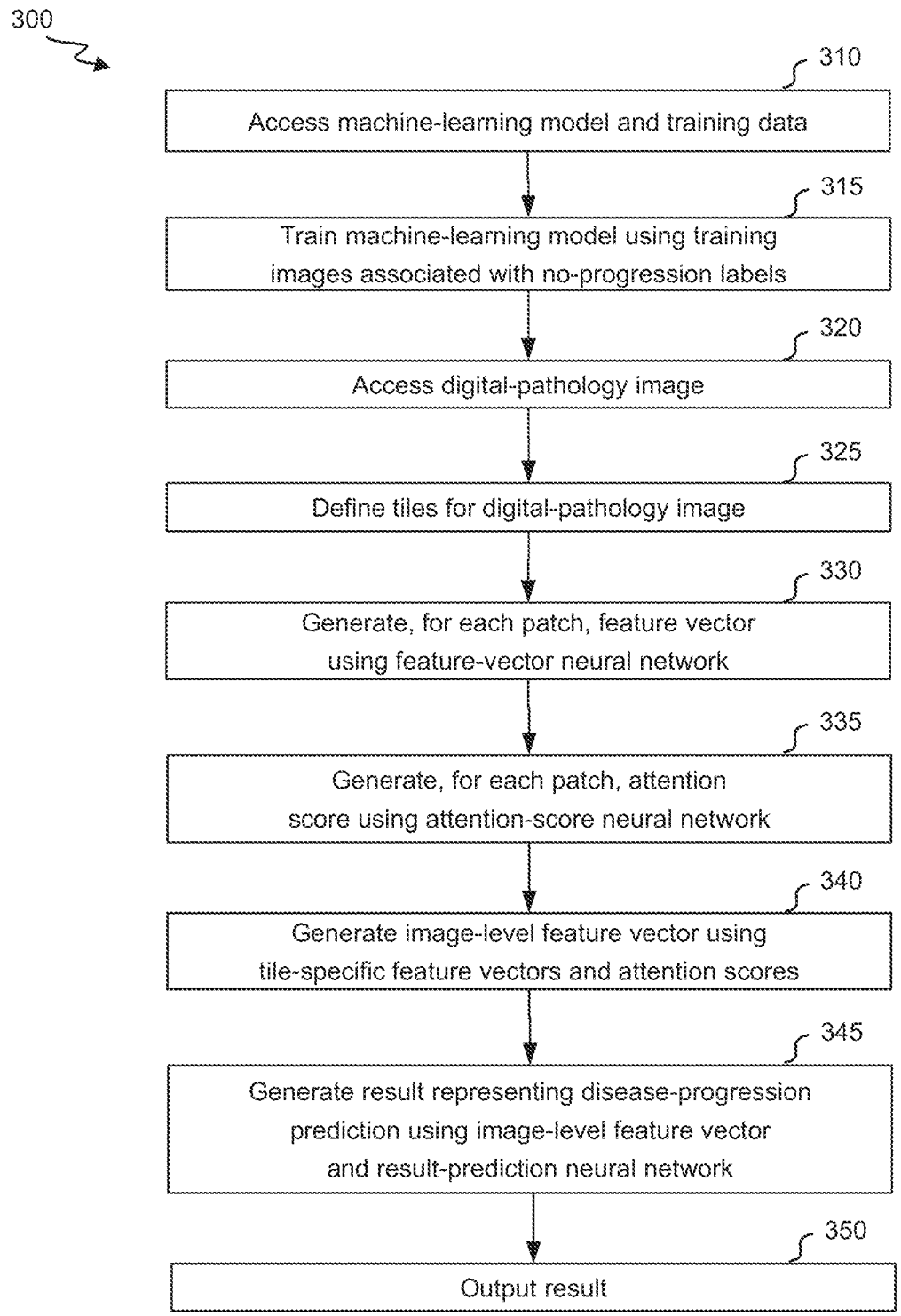
FIG. 3 shows a flowchart for an exemplary process for generating a disease-progression prediction using neural networks according to some embodiments of the present invention.

V. Exemplary Process for Using Attention-Based Techniques to Predict Disease Progression FIG. 3 shows a flowchart 300 for an exemplary process for generating a disease-progression prediction using neural networks according to some embodiments of the present invention. Process 300 may be initiated upon (automated) verification of image adequacy. An image may be verified as adequate based on, e.g., tumor content, image quality, staining quality, absence of privacy related information, etc. Process 300 begins at block 310 where training controller 165 accesses a machine-learning model and training data. The machine-learning model may include multiple neural networks. The neural networks may be configured to generate a set of patch-level feature vectors (e.g., using feature-vector network 215), to generate a set of patch-level attention scores (e.g., using attention-score network 220), and to generate an image-level result (e.g., using result-prediction network 225). The machine-learning model may aggregate the patch-level feature vectors and the patch-level attention scores to generate an image-level feature vector that may be fed to the result-prediction network to generate the image-level result. The machine-learning model can be configured to operate in the cloud, on one or more servers, and/or on a local system.

The training data can include a set of patches of digital pathology images. In some instances, each digital pathology image represented in the training data is associated with a label that indicates that a subject associated with the image did not subsequently exhibit progression within a predefined time period and/or did survive throughout a predefined time period. In some instances, each of the patches represented in the training data did not depict tumor cells. In some instances, the training data further includes one or more other images associated with a label that indicates that the subject did subsequently exhibit progression over a predefined time period and/or did not survive for at least a threshold period of time.

Each digital pathology image in the training data may have been generated by processing a sample collected from a subject. Subsequent to the collection, the subject may have received a particular treatment or no treatment. In some instances, with respect to the entire training data set, each subject represented in the training data set had been diagnosed with a same medical condition or status (e.g., diffuse B-cell lymphoma; follicular lymphoma; chronic lymphocytic leukemia; small lymphocytic lymphoma; acute myeloid leukemia; breast cancer; non-responder to R-CHOP, G-CHOP, Venetoclax-CHOP, or Polatuzumab-CHOP; etc.) and did not receive a treatment for the medical condition for at least a predefined time period beginning at a time at which a sample depicted in a corresponding image was collected (e.g., during which progression and/or survival was being monitored). In some instances, with respect to the entire training data set, each subject represented in the training data set had been diagnosed with a same medical condition or status (e.g., diffuse B-cell lymphoma; follicular lymphoma; chronic lymphocytic leukemia; small lymphocytic lymphoma; acute myeloid leukemia; breast cancer; non-responder to R-CHOP, G-CHOP, Venetoclax-CHOP, or Polatuzumab-CHOP; etc.) and received a same particular treatment for the medical condition for at least a predefined time period beginning at a time at which a sample depicted in a corresponding image was collected (e.g., during which progression and/or survival was being monitored). In some instances, with respect to the entire training data set, each subject represented in the training data set had been diagnosed with a same medical condition or status (e.g., diffuse B-cell lymphoma; follicular lymphoma; chronic lymphocytic leukemia; small lymphocytic lymphoma; acute myeloid leukemia; breast cancer; non-responder to R-CHOP, G-CHOP, Venetoclax-CHOP, Polatuzumab-CHOP; etc.) and received a standard-of-care treatment for the medical condition for at least a predefined time period beginning at a time at which a sample depicted in a corresponding image was collected (e.g., during which progression and/or survival was being monitored).

At block 315, the training controller 165 trains the machine-learning model using the training data. The training may be performed to concurrently train all of the neural networks in the machine-learning model.

At block 320, the image-processing system 135 accesses a digital pathology image. The digital pathology image accessed at block 320 may have been collected from a subject diagnosed with a same type of medical condition as the medical conditions with which subjects represented in the training data were diagnosed. The digital pathology image accessed at block 320 may include an image of a sample stained with one or more same stains as the stain(s) used to stain samples depicted in images in the training data.

In some instances, the digital pathology image is preprocessed to (for example) crop or resize the image to a target size, or modify pixel intensities (e.g., via a normalization, standardization, distribution assessment, etc.). Preprocessing may further or alternatively include changing a resolution of the digital pathology image to a target resolution.

At block 325, the patch generator 140 defines a set of patches. Each patch may correspond to a set of pixels in the digital pathology image. The patches may be overlapping with each other. In some instances, each of the set of patches is of a same size.

At block 330, for each of the set of patches, the patch-specific feature generator 145 generates a feature vector using the feature-vector neural network (e.g., trained at block 315). The feature-vector neural network can include a convolutional neural network and/or a deep neural network.

At block 335, the attention-score generator 150 generates an attention score for each patch of the set of patches using the attention-score neural network (e.g., trained at block 315). The attention-score neural network can include a feedforward network, such as a single-layer or multi-layer perceptron.

At block 340, the image-specific feature generator 155 generates an image-level feature vector using the patch-specific feature vectors and the patch-specific attention scores. For example, the image-level feature vector may be defined to be a weighted average of the patch-specific feature vectors, where the weights are set to and/or defined based on the corresponding attention scores.

At block 345, the progression predictor 160 generates a result using the image-level feature vector and the result-prediction neural network (e.g., trained at block 315). The result-prediction neural network can include a feedforward neural network, which may include one or more fully connected layers. The result may represent a predicted disease progression (e.g., if a treatment or lack of treatment received by the subject is the same as that of subjects represented in the training data). The result may include (for example) a predicted probability (e.g., numerical or categorical) or a binary prediction as to whether the subject will survive across a predefined time period if a given treatment, a given type of treatment, or if no treatment is received (e.g., throughout the time period or at the beginning of the time period). In some instances, the result-prediction neural network includes an activation function that transforms an initial output to a category or number within a particular range (e.g., 0-100 or 0-1). Additionally or alternatively, the result may represent a predicted treatment outcome.

In some instances, an output of the result-prediction neural network may be further post-processed using an activation function to generate a categorical result, binary result, or numeric result on a particular scale. In some instances, the post-processing can include transforming the output of the result-prediction neural network to identify a particular treatment to recommend or an indication as to whether the subject is eligible for a clinical study. In some instances, the post-processing can include using the output of the result-prediction neural network to stratify subjects in a clinical study.

At block 350, the image-processing system 135 outputs the result. Outputting the result can include transmitting the result. The result may be transmitted to a device or computing system associated with a care provider of the subject, of the subject, or of an entity designing a clinical study. Outputting the result can include presenting the result.

V. Examples

V.1. Exemplary Attention Scores

Figure 4:
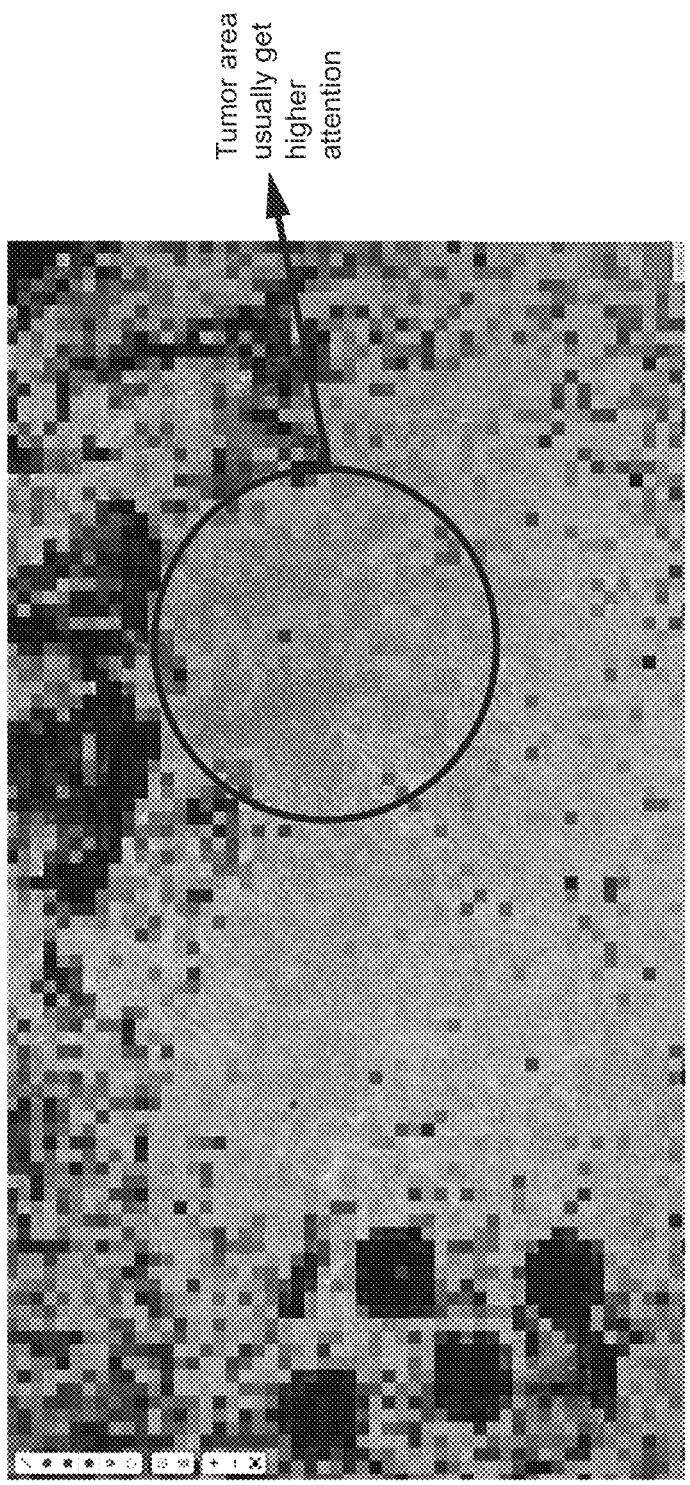
FIG. 4 illustrates an exemplary digital pathology image and corresponding attention map.

FIG. 4 illustrates an exemplary attention map. The attention map was generated based on a digital pathology image that included a WS image of a stained sample. A set of non-overlapping patches was defined for the image. An attention-score neural network was used to generate, for each patch of the set of non-overlapping patches, an attention score. Given that the patches are overlapping and due to the incremental shift between successive patches, each pixel in the digital pathology image contributed to multiple patches.

An attention-score neural network generated, for each of the set of patches, an attention score. The attention-score neural network was defined to be a multilayer fully connected perceptron. Thus, each pixel in the digital pathology image was associated with the attention score of the patch. The depicted attention map shows the attention scores across the patches. As shown in the attention map, attention scores associated with tumor regions are typically higher than attention scores associated with non-tumor regions.

It will be appreciated that, in some instances, the patches may be overlapping instead of non-overlapping. Then, each pixel in digital pathology image, as shown in FIG. 4, would be associated with multiple attention scores as a result of having been associated with multiple patches. An attention map may then be generated by determining, for each pixel, an attention-score statistic. The attention-score statistic may be defined to be the average across all of the attention scores associated with the pixel.

V.2. Exemplary Training

A machine-learning model having an architecture as depicted in FIG. 2 was configured to include multiple hyperparameters that influenced outputs of the model. The hyperparameters included dropout, risk-prediction loss weight, K-L loss weight, a threshold that differentiated between low and high risk (indicative of survival versus non-survival) and low-score loss weight and many others. The model was trained to learn risk-score differences between subjects (e.g., so as to assign higher risk scores to subjects having shorter survival periods and lower risk scores to subjects having longer survival periods) and to learn uniform attention in low-risk slides.

Particularly, the loss was defined to be a weighted sum of: (1) the risk-prediction loss (to impose a penalty when a prediction is erroneous), (2) K-L loss (to penalize K-L divergence of low-risk slides), and (3) low-score loss (to penalize high attention scores assigned to non-tumor regions, with these components being weighted with the risk-prediction loss weight, K-L loss weight, and the low-score loss weight, respectively. For example, a risk-prediction loss may impose a penalty that when risk scores do not inversely correlate with a survival time.

Training data was defined to selectively include digital pathology images associated with survival across a pre-defined time period. Training was performed to use a loss function that computed a penalty that positively correlated with a divergence between K-L divergence computed based on a distribution of attention scores associated with patches in the training data and a uniform distribution.

Figure 5B:
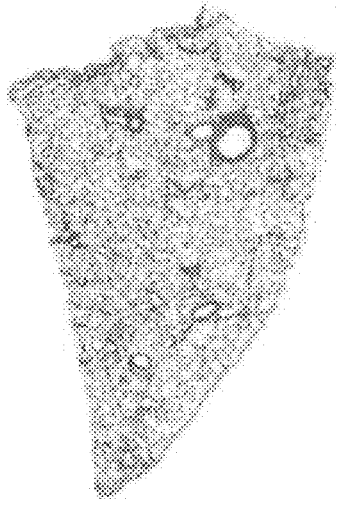
FIG. 5B illustrates an exemplary digital pathology image scaled with attention weights.
Figure 5A:
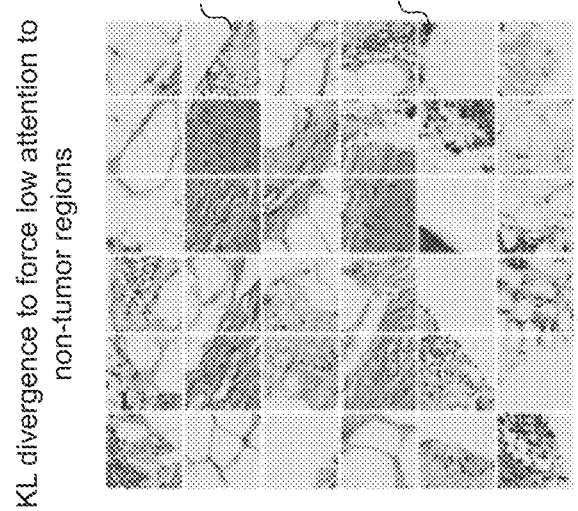
FIG. 5A illustrates exemplary patches used for training a machine-learning model, where the patches were associated with non-tumor regions.

FIG. 5A illustrates exemplary patches in the training data used for training a machine-learning model. Each of the depicted patches did not depict any tumors and/or tumor cells. The patches were obtained from multiple slides. Portions 505 correspond to stroma and/or connective tissue depictions, and portions 510 correspond to cell nuclei regions. These patches represent patches in training data that can be used to train a machine-learning model, and a loss function that penalizes variation in attention scores (and/or high attention scores) can be used. Such a loss function may result in the model paying relatively little attention to these types of patches in the inference phase.

A hypothesis is that with respect to high-risk slides and/or subjects, some patches have one or more signal and/or patch characteristics that are associated with high risk (e.g., large cells, dense cells, etc.), while low-risk slides and/or patches would not include such a signal and/or have such characteristic(s). Thus, attention scores may be used as a technique to facilitate detecting high-risk patches (which may be associated with high attention scores compared to remaining patches in the high-risk slides). On the other hand, in a low-risk slide, it would be hypothesized that the slide would lack (e.g., would not include) such high-risk patches and that relatively equal attention scores would be assigned to all patches.

FIG. 4 illustrates a weighted version of a digital pathology. For each patch of the image, an attention score was generated using an attention-score neural network.

Notably, the weighted version of the digital pathology image depicted in FIG. 5B does not include patches that are particularly pronounced with respect to other patches. This image is consistent with the attention-score neural network having been trained in a manner such that patches in images of no-progression images are assigned similar (and potentially low) weights.

V.3. Exemplary Results

A set of digital pathology images were accessed. Each digital pathology image in the image set depicted a stained sample collected from a subject who was diagnosed with diffuse B-cell lymphoma. Progression was monitored for a period of 3.9 years. If the subject experienced a disease progression event or death event within 2 years from the sample collection, the subject was associated with a "high risk" label. If the subject did not experience a disease progression or death event within 2 years from the sample collection, the subject was associated with a "low risk" label. The image data included a total of 427 low-risk subjects and 144 high-risk subjects. The training data may include more than one images per subject.

The data was split multiple times. Each split resulted in a different division of the images across training and testing data sets. Table 1 shows the split distributions for the various splits.

TABLE 1

| Split | Low risk test | High risk test | Low risk train | High risk train |
|---|---|---|---|---|
| default | 80 (0.684) | 37 (0.316) | 325 (0.696) | 142 (0.304) |
| split 0 | 82 (0.701) | 35 (0.299) | 323 (0.692) | 144 (0.308) |
| split 1 | 82 (0.701) | 35 (0.299) | 323 (0.692) | 144 (0.308) |
| split 2 | 76 (0.650) | 41 (0.350) | 329 (0.704) | 138 (0.296) |

TABLE 1-continued

| Split | Low risk test | High risk test | Low risk train | High risk train |
|---|---|---|---|---|
| split 3 | 85 (0.726) | 32 (0.274) | 320 (0.685) | 147 (0.315) |
| split 4 | 80 (0.690) | 36 (0.310) | 325 (0.694) | 143 (0.306) |

Table 2 shows results associated with multiple hyperparameter settings. With respect to the "two years AUC value": each subject was monitored to determine whether any events of interest (progression or death) were observed during a two-year time period from image collection. Area-under-the-curve (AUC) statistics were computed to compare the portion of subjects for which it was predicted that any such event was observed relative to the portion of subjects for which true observations indicated actual occurrence of any such event. The "two years AUC val" and "two years AUC test" represent this statistic calculated for the training and test data set, respectively.

Other performance metrics relate to "extreme subjects." These subjects were observed to be very high risk (who have disease progression or death of less than 150 days) or very low risk (progression-free survival of more than 1000 days). AUC values were then similarly calculated for the test and training data set.

C-index values were also generated. A C-index value is a representation based on an AUC that accounts for censored data that may influence a degree to which survival times may be reliably provided based on individual scores.

Hyperparameters associated with Configuration #10 were selected for further assessment.

progression-free survival metric represents the number of days (from the collection of the sample that was imaged) until a subject experienced some disease progression or death due to the medical condition. The overall survival metric represents the number of days (from the collection of the sample that was imaged) that the subject remained alive. For comparison, the HR (hazard ratio) with respect to FPS and OS were also computed when using IPI (international prognostic index), which is the standard method for risk prediction. Similar results were observed between the predicted metrics and the observed metrics, indicating that the model is robust.

TABLE 3

| Two years AUC Val | Two years AUC Test | Extreme AUC Val | Extreme AUC Test | C index Val | C index Test | HR PFS Val | HR PFS Test | HR OS Val | HR OS Test |
|---|---|---|---|---|---|---|---|---|---|
| 0.640972 | 0.694779 | 0.751323 | 0.847222 | 0.608196 | 0.641465 | 0.346023 | 0.350419 | 0.325237 | 0.215033 |

Table 4 shows additional hyperparameters selected to generate the results.

TABLE 4

| Hyperparameter | Value |
|---|---|
| No. max epochs | 200 |
| Learning rate | Fixed at 0.001 |
| Patch size | 256 |
| Batch size | 128 |
| Bag sample size | 128 |
| Drop-out rate | 0.7 |
| K-L divergence loss weight | 5 |
| Low risk threshold | 800 |
| Low attention loss weight | 0 |

For each training-testing data split, a best-performing epoch was selected as the epoch that was associated with the

TABLE 2

| Param Configuration | dropout | kl loss weight | low risk threshold | low score loss eight | Best performing epoch | Two years AUC Val | Two years AUC Test | Extreme AUC Val | Extreme AUC Test | C index Val |
|---|---|---|---|---|---|---|---|---|---|---|
| Config 0 | 0.6 | 2 | 1000 | 0 | 10 | 0.65731 | 0.632753 | 0.78836 | 0.756944 | 0.635908 |
| Config 1 | 0.6 | 1 | 1000 | 0 | 23 | 0.645999 | 0.663989 | 0.785714 | 0.864167 | 0.617336 |
| Config 2 | 0.6 | 0.1 | 1000 | 0 | 10 | 0.650607 | 0.636323 | 0.753968 | 0.784722 | 0.630896 |
| Config 3 | 0.6 | 0.5 | 1000 | 0.1 | 12 | 0.624633 | 0.609996 | 0.769259 | 0.697917 | 0.608196 |
| Config 4 | 0.6 | 1 | 1000 | 0.1 | 30 | 0.634269 | 0.636323 | 0.814815 | 0.8125 | 0.606722 |
| Config 5 | 0.6 | 1 | 1000 | 0.5 | 13 | 0.705488 | 0.61178 | 0.791005 | 0.684028 | 0.657134 |
| Config 6 | 0.7 | 0.2 | 1000 | 0 | 43 | 0.677 | 0.655511 | 0.785714 | 0.798611 | 0.640625 |
| Config 7 | 0.6 | 1 | 800 | 0 | 44 | 0.643486 | 0.624721 | 0.812169 | 0.8125 | 0.611439 |
| Config 8 | 0.6 | 0.2 | 800 | 0 | 25 | 0.634269 | 0.664436 | 0.780423 | 0.850694 | 0.610554 |
| Config 9 | 0.6 | 5 | 1000 | 0 | 9 | 0.648513 | 0.620705 | 0.769841 | 0.736111 | 0.622936 |
| Config 10 | 0.7 | 5 | 800 | 0 | 52 | 0.640972 | 0.694779 | 0.751323 | 0.847222 | 0.608196 |
| Config 11 | 0.7 | 100 | 800 | 0 | 44 | 0.635526 | 0.691656 | 0.714286 | 0.836806 | 0.607017 |
| Config 12 | 0.7 | 100 | 800 | 0 | 44 | 0.635526 | 0.691656 | 0.714286 | 0.836806 | 0.607017 |
| Config 13 | 0.7 | 100 | 500 | 0 | 71 | 0.638877 | 0.698795 | 0.716931 | 0.868056 | 0.605542 |
| Config 14 | 0.2 | 5 | 800 | 0 | 21 | 0.658986 | 0.598394 | 0.804233 | 0.819444 | 0.614682 |
| Config 15 | 0.7 | 5 | 500 | 0 | 49 | 0.634688 | 0.699241 | 0.740741 | 0.868058 | 0.602005 |
| Config 16 | 0.4 | 100 | 500 | 0 | 15 | 0.626728 | 0.652387 | 0.806878 | 0.84375 | 0.604068 |
| Config 17 | 0.4 | 5 | 500 | 0 | 60 | 0.635945 | 0.605979 | 0.767196 | 0.753472 | 0.600236 |

Table 3 shows results generated using the Configuration 10 hyperparameters. In addition to the above-described results, Table 3 includes progression-free survival (PFS) metrics and overall survival (OS) metrics. The PFS and OS metrics were generated for both a training and testing data set. The highest two year AUC value for the validation set and that gave a training C-index that was greater than 0.65. Table 5 shows the results of 5 splits and the average across the splits. The values in Table 5 indicate that the model's performance is lower for splits 1 and 2 relative to splits 0 and 4, which indicates the high variability in the dataset. Potentially, subject data included confounding variables that affected the PFS but that were not represented in the digital pathology images.

TABLE 5

| Test Split | Best performing epoch | Two years AUC Val | Two years AUC Test | Extreme AUC Val | Extreme AUC Test | C indix Val | C index Test | HR PFS Val | HR PFS Test | HR OS Val |
|---|---|---|---|---|---|---|---|---|---|---|
| Split 0 | 130 | 0.587979 | 0.650233 | 0.647619 | 0.65102 | 0.563502 | 0.626752 | 0.765386 | 0.191987 | 0.738817 |
| Split 1 | 46 | 0.669686 | 0.5225 | 0.935897 | 0.4 | 0.652955 | 0.494663 | 0.428245 | 1.038435 | 0.387657 |
| Split 2 | 50 | 0.616531 | 0.498115 | 0.734247 | 0.62212 | 0.614767 | 0.501818 | 0.474123 | 1.34157 | 0.452121 |
| Split 3 | 195 | 0.461207 | 0.630087 | 0.323413 | 0.811404 | 0.455162 | 0.629307 | 1.62676 | 0.499275 | 1.727215 |
| Split 4 | 100 | 0.495483 | 0.656867 | 0.472222 | 0.73913 | 0.49829 | 0.600578 | 0.8507724 | 0.648925 | 1.094047 |
| Average | 104.2 | 0.566177 | 0.59156 | 0.62268 | 0.644735 | 0.556935 | 0.570624 | N/A | N/A | N/A |

IV. Additional Considerations

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

The description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

What is claimed is:

1. A computer-implemented method for using machine learning to process digital pathology images to predict disease progression, the method comprising:
    accessing a digital pathology image that depicts a specimen stained with one or more stains, the specimen having been collected from a subject;
    defining a set of patches for the digital pathology image, wherein each patch of the set of patches depicts a portion of the digital pathology image;
    generating, for each patch of the set of patches and using an attention-score neural network, an attention score, wherein the attention-score neural network is trained using a loss function, the loss function penalizes attention-score variability across patches in training digital pathology images, the training digital pathology images labeled to indicate subsequent disease progression has occurred;
    generating, using a result-prediction neural network and the attention scores, a result representing a prediction of whether or an extent to which a disease of the subject will progress; and
    outputting the result.

2. The computer-implemented method of claim 1, further comprising:
    generating, for each patch of the set of patches and using a feature-vector neural network, a feature vector for the patch, wherein the result further depends on the feature vectors for the set of patches.

3. The computer-implemented method of claim 2, wherein the result is an image-based output generated based on the feature vectors and the attention scores for the set of patches.

4. The computer-implemented method of claim 2, wherein the generating the result includes:
    generating a cross-patch feature vector using the feature vectors and the attention scores for the set of patches; and
    generating the result by processing the cross-patch feature vector using the result-prediction neural network.

5. The computer-implemented method of claim 2, wherein the feature vectors for the set of patches represent cell nuclei regions, wherein the generating the result further comprises:
    performing nuclei detection and segmentation to segment the set of patches into cell nuclei and non-cell nuclei regions;
    performing nuclei classification to identify individual cell nucleus from a nuclei segmentation mask;
    calculating cellular features from the set of patches and the nuclei segmentation mask; and
    calculating one or more patch-level metrics to form a patch-level representation, wherein the one or more patch-level metrics represent feature distribution of the cell nuclei regions.

6. The computer-implemented method of claim 2, wherein the feature-vector neural network includes a convolutional neural network.

7. The computer-implemented method of claim 1, wherein the loss function is configured to depend on multiple terms, wherein at least one of the multiple terms depends on an accuracy of the prediction and a second term defined.

8. The computer-implemented method of claim 1, wherein the loss function is defined using a K-L divergence technique.

9. The computer-implemented method of claim 1, wherein the loss function is configured such that a penalty depends on a degree of non-uniformity across the attention scores generated for the patches in the training digital pathology images labeled to indicate subsequent disease progression has occurred.

10. The computer-implemented method of claim 1, wherein the attention-score neural network includes a perceptron neural network.

11. The computer-implemented method of claim 1, wherein the attention-score neural network is trained using a training data set in which at least 90% of the training digital pathology images were labeled to indicate subsequent disease progression has occurred.

12. The computer-implemented method of claim 1, wherein the result represents a high likelihood of the disease of the subject progressing by at least a predefined threshold amount within a predefined period of time.

13. The computer-implemented method of claim 1, wherein the result further includes an identification of a subset of the set of patches that were more influential than other patches in the set of patches in the generation of result.

14. The computer-implemented method of claim 1, wherein the loss function further penalizes a lack of cross-portion variation in the attention scores in the training digital pathology images associated with no disease progression.

15. The computer-implemented method of claim 1, wherein the disease is at least one of: diffuse B-cell lymphoma, follicular lymphoma, chronic lymphocytic leukemia, small lymphocytic lymphoma, acute myeloid leukemia, or breast cancer.

16. A system for using machine learning to process digital pathology images to predict disease progression, the system comprising one or more data processors, memory, and one or more programs stored in the memory for execution by the one or more processors and including instructions for:
    accessing a digital pathology image that depicts a specimen stained with one or more stains, the specimen having been collected from a subject;
    defining a set of patches for the digital pathology image, wherein each patch of the set of patches depicts a portion of the digital pathology image;
    generating, for each patch of the set of patches and using an attention-score neural network, an attention score, wherein the attention-score neural network is trained using a loss function, the loss function penalizes attention-score variability across patches in training digital pathology images, the training digital pathology images labeled to indicate subsequent disease progression has occurred;
    generating, using a result-prediction neural network and the attention scores, a result representing a prediction of whether or an extent to which a disease of the subject will progress; and
    outputting the result.

17. The system of claim 16, wherein the one or more programs include further instructions for generating, for each patch of the set of patches and using a feature-vector neural network, a feature vector for the patch, wherein the result further depends on the feature vectors for the set of patches.

18. The system of claim 17, wherein the result is an image-based output generated based on the feature vectors and the attention scores for the set of patches.

19. The system of claim 17, wherein the generating the result includes:
    generating a cross-patch feature vector using the feature vectors and the attention scores for the set of patches; and
    generating the result by processing the cross-patch feature vector using the result-prediction neural network.

20. The system of claim 17, wherein the feature vectors for the set of patches represent cell nuclei regions, wherein the generating the result further comprises:
    performing nuclei detection and segmentation to segment the set of patches into cell nuclei and non-cell nuclei regions;
    performing nuclei classification to identify individual cell nucleus from a nuclei segmentation mask;
    calculating cellular features from the set of patches and the nuclei segmentation mask; and
    calculating one or more patch-level metrics to form a patch-level representation, wherein the one or more patch-level metrics represent feature distribution of the cell nuclei regions.

21. The system of claim 16, wherein the feature-vector neural network includes a convolutional neural network.

22. The system of claim 16, wherein the loss function is configured to depend on multiple terms, wherein at least one of the multiple terms depends on an accuracy of the prediction and a second term defined.

23. The system of claim 16, wherein the loss function is defined using a K-L divergence technique.

24. The system of claim 16, wherein the loss function is configured such that a penalty depends on a degree of non-uniformity across the attention scores generated for the patches in the training digital pathology images labeled to indicate subsequent disease progression has occurred.

25. The system of claim 16, wherein the attention-score neural network is trained using a training data set in which at least 90% of the training digital pathology images were labeled to indicate subsequent disease progression has occurred.

26. The system of claim 16, wherein the result represents a high likelihood of the disease of the subject progressing by at least a predefined threshold amount within a predefined period of time.

27. The system of claim 16, wherein the result further includes an identification of a subset of the set of patches that were more influential than other patches in the set of patches in the generation of result.

28. The system of claim 16, wherein the loss function further penalizes a lack of cross-portion variation in the attention scores in the training digital pathology images associated with no disease progression.

29. The system of claim 16, wherein the disease is at least one of: diffuse B-cell lymphoma, follicular lymphoma, chronic lymphocytic leukemia, small lymphocytic lymphoma, acute myeloid leukemia, or breast cancer.

30. A computer-program product tangibly embodied in a non-transitory machine-readable storage medium, including instructions configured to cause one or more data processors to perform:
- accessing a digital pathology image that depicts a specimen stained with one or more stains, the specimen having been collected from a subject;
- defining a set of patches for the digital pathology image, wherein each patch of the set of patches depicts a portion of the digital pathology image;
- generating, for each patch of the set of patches and using an attention-score neural network, an attention score, wherein the attention-score neural network is trained using a loss function, the loss function penalizes attention-score variability across patches in training digital pathology images, the training digital pathology images labeled to indicate subsequent disease progression has occurred;
- generating, using a result-prediction neural network and the attention scores, a result representing a prediction of whether or an extent to which a disease of the subject will progress; and
- outputting the result.

\* \* \* \* \*